United States Patent [19]

Enami et al.

[11] Patent Number: 5,077,420

[45] Date of Patent: Dec. 31, 1991

[54] ORGANOSILICON COMPOUNDS AND METHOD FOR THEIR PREPARATION

[75] Inventors: Hiroji Enami; Takeshi Imai, both of Ichihara, Japan

[73] Assignee: Dow Corning Toray Silicone Company, Ltd., Tokyo, Japan

[21] Appl. No.: 539,261

[22] Filed: Jun. 18, 1990

[30] Foreign Application Priority Data

Jul. 12, 1989 [JP] Japan ................................. 1-179474

[51] Int. Cl.$^5$ ........................... C07F 7/10; C07F 7/18
[52] U.S. Cl. .................................. 556/413; 556/423; 556/424
[58] Field of Search ........................ 556/413, 423, 424

[56] References Cited

U.S. PATENT DOCUMENTS

| | | | |
|---|---|---|---|
| 3,627,800 | 12/1971 | Owen et al. | 556/424 |
| 4,254,270 | 3/1981 | Kötzsch et al. | 556/424 X |
| 4,744,812 | 5/1988 | Parg et al. | 556/423 X |
| 4,804,653 | 2/1989 | Strunk et al. | 556/423 X |
| 4,948,858 | 8/1990 | Barthelemy | 556/423 X |

*Primary Examiner*—Paul F. Shaver
*Attorney, Agent, or Firm*—William F. Boley

[57] ABSTRACT

The present invention relates to novel alkylamino-substituted organosilicon compounds and a method for their preparation. The described process involves a dehydrohalogenation reaction between a triorganosilylalkyl halide and an aminophenol in the presence of a hydrogen halide acceptor.

3 Claims, No Drawings

ORGANOSILICON COMPOUNDS AND METHOD FOR THEIR PREPARATION

BACKGROUND OF INVENTION

The present invention relates to novel organosilicon compounds, and, more particularly, relates to alkylaminophenol-substituted organosilicon compounds and a method for their preparation.

Alkylphenol-substituted organosilicon compounds are known, for example, from Japanese Patent Publication Number 41-11097 (11,097/66); however, alkylaminophenol-substituted organosilicon compounds are heretofore unknown.

The present invention takes as its object the introduction of novel organosilanes in the form of alkylaminophenol-substituted organosilicon compounds and their quaternary ammonium salts, as well as the introduction of a method for their preparation.

The organosilicon compounds of the present invention as described above have potential applications as silane coupling agents. Thus, it is possible to improve the mechanical and electrical properties of various plastics by their mixture with the organosilicon compounds of the present invention. The organosilicon compounds of the present invention are also useful as surface treatment agents for glass fibers and inorganic materials.

DESCRIPTION OF INVENTION

The present invention comprises organosilicon compounds as represented by general formula

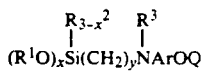

wherein $R^1$ and $R^2$ are the same or different monovalent hydrocarbon group(s) having 1 to 6 carbon atoms, $R^3$ is a hydrogen atom or a monovalent hydrocarbon group having 1 to 6 carbon atoms, Ar is an organic group selected from a group consisting of

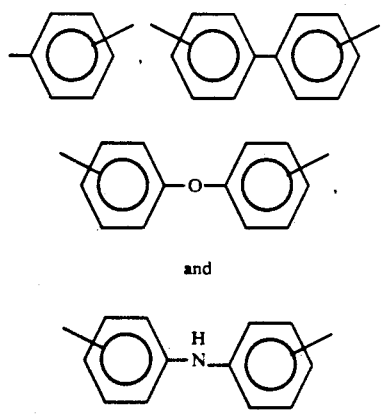

Q is a hydrogen atom or a trialkylsilyl group as represented by —SiR$^4{}_3$ wherein $R^4$ is an alkyl group having 1 to 6 carbon atoms, x is an integer with a value of 1 to 3, and y is an integer with a value of 1 to 6; and the quaternary ammonium salts of said organosilicon compounds.

In addition, the present invention also comprises organosilicon compounds as represented by general formula

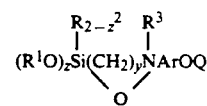

wherein $R^1$ and $R^2$ are the same or different monovalent hydrocarbon group(s) having 1 to 6 carbon atoms, Ar is an organic group selected from a group consisting of

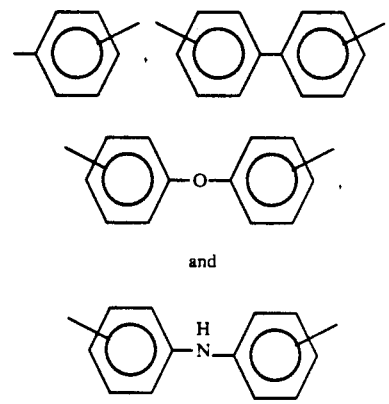

Q is a hydrogen atom or a trialkylsilyl group as represented by —SiR$^4{}_3$, wherein $R^4$ is an alkyl group having 1 to 6 carbon atoms, y is an integer with a value of 1 to 6, and z is an integer with a value of 1 to 2; and the quaternary ammonium salts of said organosilicon compounds.

To explain the preceding in greater detail, the groups $R^1$ and $R^2$ in the above formulas for the organosilicon compounds of the present invention comprise monovalent hydrocarbon groups as illustrated by alkyl groups such as methyl, ethyl, propyl, butyl, and so forth. $R^3$ comprises the hydrogen atom and monovalent hydrocarbon groups having 1 to 6 carbon atoms as illustrated by alkyl groups such as methyl, ethyl, propyl, butyl, and so forth, and by aryl groups such as phenyl. Ar is an organic group selected from a group consisting of

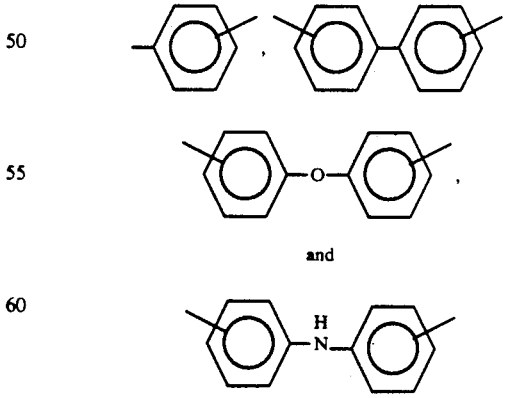

and Q is a hydrogen atom or a trialkylsilyl group as represented by —SiR$^4{}_3$, wherein $R^4$ is an alkyl group having 1 to 6 carbon atoms as exemplified by methyl, ethyl, propyl, and so forth.

The following are provided as concrete examples of the organosilicon compounds under consideration.

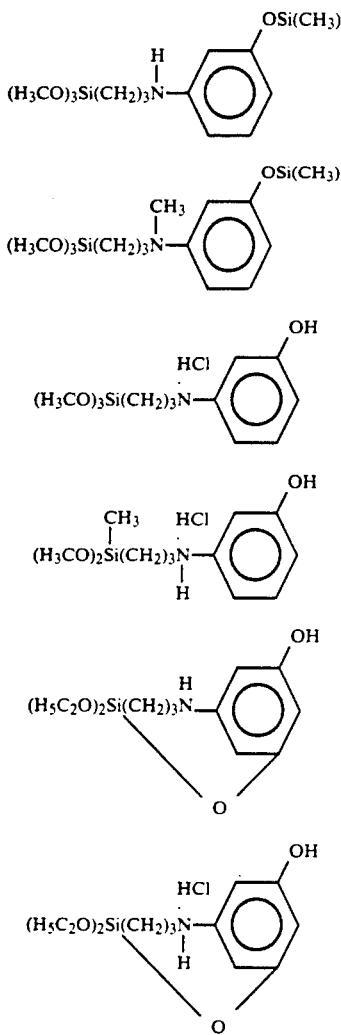

The organosilicon compounds of the present invention can be prepared by, for example, the method described below.

This method comprises the execution of a dehydrohalogenation reaction between (A) a triorganosilylalkyl halide as represented by general formula

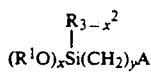

wherein $R^1$ and $R^2$ represent the same or different monovalent hydrocarbon group(s) having 1 to 6 carbon atoms; A is a halogen atom selected from a group consisting of fluorine atom, chlorine atom, bromine atom, and iodine atom; x is an integer with a value of 1 to 3; and y is an integer with a value of 1 to 6; and (B) an aminophenol as represented by general formula

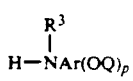

wherein Q is a hydrogen atom or a trialkylsilyl group represented by $-SiR^4{}_3$, in which $R^4$ is an alkyl group having 1 to 6 carbon atoms, Ar is an organic group selected from a group consisting of

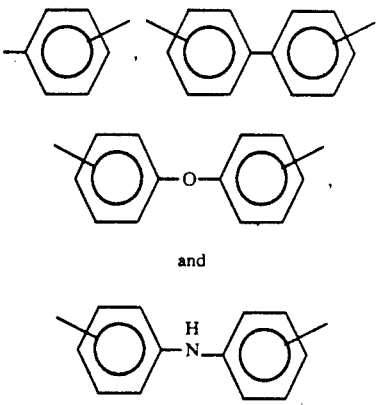

$R^3$ is a hydrogen atom or a monovalent hydrocarbon group having 1 to 6 carbon atoms, and p is an integer with a value of 1 to 2; in the presence of (C) a hydrogen halide acceptor.

The triorganosilylalkyl halide or derivative thereof comprising the component (A) used by this method is the main starting material for the synthesis of the organosilicon compounds of the present invention. The groups $R^1$, $R^2$, and $R^3$ in the preceding formula have the same definitions, respectively, as the groups $R^1$, $R^2$, and $R^3$ in the above-defined organosilicon compounds of the present invention. The organosilicon compounds comprising this component (A) are commercially available. Examples of such organosilicon compounds are gamma-chloropropyltrimethoxysilane and gamma-chloropropylmethyldimethoxysilane.

The aminophenol or derivative thereof comprising the component (B) used by this method participates in a dehydrohalogenation reaction with the above component (A) in the presence of a hydrogen halide acceptor to afford the organosilicon compounds of the present invention. Among such compounds (B), the following are commercially available: m-aminophenol, o-aminophenol, and p-aminophenol.

The hydrogen halide acceptor comprising the component (C) used in the present method encompasses tertiary amines such as triethylamine, pyridine, and so forth; secondary amines such as dimethylamine, diethylamine, and so forth; primary amines such as methylamine, ethylamine, and so forth; ammonia; and conjugate bases such as sodium carbonate, potassium carbonate, and so forth.

The reaction under consideration will proceed even in the absence of a solvent, but running the reaction in an organic solvent is generally preferred. While no specific restriction is placed on the organic solvent, polar solvents are particularly suitable, for example, amides such as N,N-dimethylformamide, N-methylpyrrolidone, and so forth, as well as dimethyl sulfoxide, and hexamethylphosphonamide.

Furthermore, the reaction temperature is closely related to the reaction rate in the present case, and the reaction is completed more rapidly at higher temperatures. However, side reactions readily occur when the reaction temperature is too high, and an appropriate temperature must be selected on balance. In concrete terms, this reaction is preferably conducted within the temperature range of 80 to 130 degree Centigrade.

The molecular structure of the organosilicon compounds of the present invention can be confirmed by various analytic methods. For example, nuclear magnetic resonance spectral analysis, infrared absorption spectral analysis, ultraviolet absorption spectral analysis, etc., are very fruitful techniques for determining, inter alia, the atomic arrangement and substitution pattern of the organosilicon compounds of the present invention. Elemental analysis and gas chromatographic analysis, etc., are good techniques for measuring the purity.

The present invention is explained below in greater detail by illustrative examples, in which the term parts refers to weight parts.

EXAMPLE 1

62.6 Parts gamma-chloropropyltrimethoxysilane and 32.7 parts m-aminophenol were introduced into and mixed in a stirrer-equipped reactor. The temperature was raised and the reaction was stirred with heating at 110 degrees Centigrade for 6 hours. After cooling, 68.8 parts methanol was added to the obtained reaction mixture, which was then stirred for 2 hours while heating at 40 degrees Centigrade. 217 Parts hexamethyldisilazane was subsequently dripped in over 3 hours at 50 degrees Centigrade. The ammonium chloride by-product was then filtered off and the obtained filtrate was distilled, and 61.0 parts of a fraction at 143 to 144 degrees Centigrade/16 mmHg was taken off. This fraction consisted of a light yellow, transparent liquid, and its yield was 59.0%.

The molecular structure of this liquid was confirmed as 3-(3-trimethylsiloxyanilino)propyltrimethoxysilane, by nuclear magnetic resonance spectral analysis and infrared absorption spectral analysis.

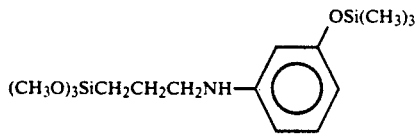

EXAMPLE 2

57.6 Parts gamma-chloropropylmethyldimethoxysilane and 32.7 parts m-aminophenol were mixed in a dried reactor and heated at 100 degrees Centigrade with stirring for 8 hours. After cooling, 68.8 parts methanol was added to the reaction solution, followed by heating at 40 degrees Centigrade with stirring for 3 hours.

Based on nuclear magnetic resonance spectral analysis and infrared absorption spectral analysis, the obtained reaction product was confirmed to be (3-(3-hydroxyanilino)propylmethyldimethoxysilane) hydrochloride with the following molecular structure.

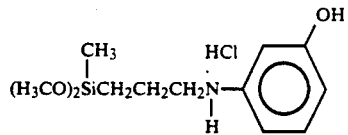

What is claimed is:

1. Organosilicon compounds comprising general formula

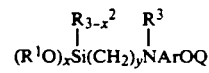

wherein $R^1$ and $R^2$ are monovalent hydrocarbon groups having 1 to 6 carbon atoms, $R^3$ is a hydrogen atom or a monovalent hydrocarbon group having 1 to 6 carbon atoms, Ar is an organic group selected from a group consisting of

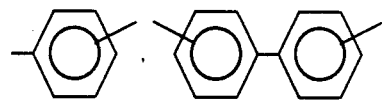

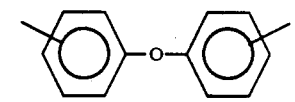

and

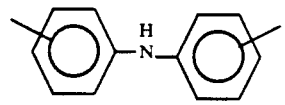

Q is a hydrogen atom or a trialkylsilyl group as represented by $-SiR^4_3$, wherein $R^4$ is an alkyl group having 1 to 6 carbon atoms, x is an integer with a value of 1 to 3, and y is an integer with a value of 1 to 6; and quaternary ammonium salts of said organosilicon compounds.

2. The organosilicon compound of claim 1, wherein x is 3, $R^1$ is a methyl radical, and Q is a trimethylsilyl radical.

3. The organosilicon compound of claim 1, wherein x is 2, $R^1$ and $R^2$ are methyl radicals, and Q is a hydrogen atom.

* * * * *